United States Patent [19]

Frank et al.

[11] Patent Number: 5,830,637
[45] Date of Patent: Nov. 3, 1998

[54] APPARATUS AND METHODS FOR DETECTING ANTIBODIES

[75] Inventors: Ronald Frank; Sinan Guler, both of Brunswick, Germany

[73] Assignee: Gesellschaft fur Biotechnologische Forschung mbH (GBF), Brunswick, Germany

[21] Appl. No.: 724,548

[22] Filed: Sep. 30, 1996

Related U.S. Application Data

[62] Division of Ser. No. 978,674, filed as PCT/EP91/01529, Dec. 8, 1991.

[30] Foreign Application Priority Data

Aug. 31, 1990 [DE] Germany ............... P 40 27 675/9

[51] Int. Cl.$^6$ .................... C12Q 1/70; G01N 33/53; C07K 1/04
[52] U.S. Cl. .................. 435/5; 435/7.1; 436/501; 422/104; 530/334
[58] Field of Search ................. 422/104; 435/5, 435/6, 7.1; 530/333, 334; 536/25.3; 436/501

[56] References Cited

U.S. PATENT DOCUMENTS

| | | | |
|---|---|---|---|
| 5,143,854 | 9/1992 | Pirrung et al. | 436/518 |
| 5,429,807 | 7/1995 | Matson et al. | 422/131 |
| 5,436,327 | 7/1995 | Southern et al. | 536/25.34 |

FOREIGN PATENT DOCUMENTS

| | | | |
|---|---|---|---|
| 89/10977 | 11/1989 | WIPO | C12Q 1/68 |

*Primary Examiner*—Kenneth R. Horlick
*Attorney, Agent, or Firm*—Kane, Dalsimer, Sullivan, Kurucz, Levy, Eisele and Richard

[57] ABSTRACT

A single, unitary, solid phase support apparatus having a planar surface divided into a plurality of separate zone functions to detect antibodies. Each zone has bonded to it, a different peptide through its C-terminal end. The zones are incubated with the analyte sample and observed for reaction, indicating the virus-specific or bacteria specific presence or absence.

9 Claims, 11 Drawing Sheets

CMV26 (36/40K protein)

Ala Arg Gly Ser Xaa Glu Arg Gly Lys Ser Arg Gly Gly
Gly Gly Gly Gly Gly Ser Leu Ser Ser Leu Ala
Xaa Ala Gly Gly Leu Asn Asp Asp Gly Pro Gly
Asp Xaa Asp Leu Met Xaa Glu Pro Met Gly Leu
Gly Gly Leu Gly Gly Gly Gly Gly Gly Gly Lys Lys
His Leu Asp Pro Ser Thr Cys Ser Gln Ala Cys

FIG. 1

| | | LEN | M. W. | PROTECTION / MODIFICATION |
|---|---|---|---|---|
| 1 - 1A | Lie - Glu - Gly - Arg - Gly - Lys - Ser - Arg - Gly - Gly | 10 | 1015.6 | |
| 2 - 2A | Glu - Gly - Arg - Gly - Lys - Ser - Arg - Gly - Gly - Gly | 10 | 959.6 | |
| 3 - 3A | Gly - Arg - Gly - Lys - Ser - Arg - Gly - Gly - Gly - Gly | 10 | 887.6 | |
| 4 - 4A | Arg - Gly - Lys - Ser - Arg - Gly - Gly - Gly - Gly - Gly | 10 | 887.6 | |
| 5 - 5A | Gly - Lys - Ser - Arg - Gly - Gly - Gly - Gly - Gly - Gly | 10 | 788.5 | |
| 6 - 6A | Lys - Ser - Arg - Gly - Gly - Gly - Gly - Gly - Gly - Gly | 10 | 788.5 | |
| 7 - 7A | Ser - Arg - Gly - Gly - Gly - Gly - Gly - Gly - Gly - Ser | 10 | 747.4 | |
| 8 - 8A | Arg - Gly - Gly - Gly - Gly - Gly - Gly - Gly - Ser - Leu | 10 | 773.5 | |
| 9 - 9A | Gly - Gly - Gly - Gly - Gly - Gly - Gly - Ser - Leu - Ser | 10 | 704.4 | |
| 10 - 10A | Gly - Gly - Gly - Gly - Gly - Gly - Ser - Leu - Ser - Ser | 10 | 734.4 | |
| 11 - 11A | Gly - Gly - Gly - Gly - Gly - Ser - Leu - Ser - Ser - Leu | 10 | 790.5 | |
| 12 - 12A | Gly - Gly - Gly - Gly - Ser - Leu - Ser - Ser - Leu - Ala | 10 | 804.5 | |
| 13 - 13A | Gly - Gly - Gly - Ser - Leu - Ser - Ser - Leu - Ala - Xaa | 10 | 861.5 | |

FIG. 2A

| | | |
|---|---|---|
| 14 - 14A | 10 | 875.5 |
| | Gly - Gly - Ser - Leu - Ser - Ser - Leu - Ala - Xaa - Ala | |
| 15 - 15A | 10 | 875.5 |
| | Gly - Ser - Leu - Ser - Ser - Leu - Ala - Xaa - Ala - Gly | |
| 16 - 16A | 10 | 875.5 |
| | Ser - Leu - Ser - Ser - Leu - Ala - Xaa - Ala - Gly - Gly | |
| 17 - 17A | 10 | 901.6 |
| | Leu - Ser - Ser - Leu - Ala - Xaa - Ala - Gly - Gly - Leu | |
| 18 - 18A | 10 | 925.6 |
| | Ser - Ser - Leu - Ala - Xaa - Ala - Gly - Gly - Leu - His | |
| 19 - 19a | 10 | 953.6 |
| | Ser - Leu - Ala - Xaa - Ala - Gly - Gly - Leu - His - Asp | |
| 20 - 20A | 10 | 981.5 |
| | Leu - Ala - Xaa - Ala - Gly - Gly - Leu - His - Asp - Asp | |
| 21 - 21A | 10 | 925.5 |
| | Ala - Xaa - Ala - Gly - Gly - Leu - His - Asp - Asp - Gly | |
| 22 - 22a | 10 | 951.5 |
| | Xaa - Ala - Gly - Gly - Leu - His - Asp - Asp - Gly - Pro | |
| 23 - 23A | 10 | 894.5 |
| | Ala - Gly - Gly - Leu - His - Asp - Asp - Gly - Pro - Gly | |
| 24 - 24A | 10 | 936.5 |
| | Gly - Gly - Leu - His - Asp - Asp - Gly - Pro - Gly - Leu | |
| 25 - 25A | 10 | 994.5 |
| | Gly - Leu - His - Asp - Asp - Gly - Pro - Gly - Leu - Asp | |
| 26 - 26A | 10 | 1051.6 |
| | Leu - His - Asp - Asp - Gly - Pro - Gly - Leu - Asp - Xaa | |
| 27 - 27A | 10 | 1053.5 |
| | His - Asp - Asp - Gly - Pro - Gly - Leu - Asp - Xaa - Asp | |

FIG. 2B

| | | 10 | 1029.5 | |
|---|---|---|---|---|
| 28 - 28A | | | | |
| | Asp - Asp - Gly - Pro - Gly - Leu - Asp - Xaa - Asp - Leu | | | |
| 29 - 29A | | 10 | 1045.5 | |
| | Asp - Gly - Pro - Gly - Leu - Asp - Xaa - Asp - Leu - Met | | | |
| 30 - 30A | | 10 | 1044.5 | |
| | Gly - Pro - Gly - Leu - Asp - Xaa - Asp - Leu - Met - Xaa | | | |
| 31 - 31A | | 10 | 1116.6 | |
| | Pro - Gly - Leu - Asp - Xaa - Asp - Leu - Met - Xaa - Glu | | | |
| 32 - 32a | | 10 | 1116.6 | |
| | Gly - Leu - Asp - Xaa - Asp - Leu - Met - Xaa - Glu - Pro | | | |
| 33 - 33A | | 10 | 1190.6 | |
| | Leu - Asp - Xaa - Asp - Leu - Met - Xaa - Glu - Pro - Met | | | |
| 34 - 34A | | 10 | 1134.5 | |
| | Asp - Xaa - Asp - Leu - Met - Xaa - Glu - Pro - Met - Gly | | | |
| 35 - 35A | | 10 | 1132.6 | |
| | Xaa - Asp - Leu - Met - Xaa - Glu - Pro - Met - Gly - Leu | | | |
| 36 - 36A | | 10 | 1075.6 | |
| | Asp - Leu - Met - Xaa - Glu - Pro - Met - Gly - Leu - Gly | | | |
| 37 - 37A | | 10 | 1017.6 | |
| | Leu - Met - Xaa - Glu - Pro - Met - Gly - Leu - Gly - Gly | | | |
| 38 - 38a | | 10 | 1017.6 | |
| | Met - Xaa - Glu - Pro - Met - Gly - Leu - Gly - Gly - Leu | | | |
| 39 - 39A | | 10 | 943.5 | |
| | Xaa - Glu - Pro - Met - Gly - Leu - Gly - Gly - Leu - Gly | | | |
| 40 - 40A | | 10 | 886.5 | |
| | Glu - Pro - Met - Gly - Leu - Gly - Gly - Leu - Gly - Gly | | | |
| 41 - 41A | | 10 | 814.5 | |
| | Pro - Met - Gly - Leu - Gly - Gly - Leu - Gly - Gly - Gly | | | |

FIG. 2C

| | | | |
|---|---|---|---|
| 42 - 42A | | 10 | 774.5 |
| | Met - Gly - Leu - Gly - Gly - Leu - Gly - Gly - Gly - Gly | | |
| 43 - 43A | | 10 | 700.4 |
| | Gly - Leu - Gly - Gly - Leu - Gly - Gly - Gly - Gly | | |
| 44 - 44A | | 10 | 700.4 |
| | Leu - Gly - Gly - Leu - Gly - Gly - Gly - Gly - Gly | | |
| 45 - 45A | | 10 | 644.4 |
| | Gly - Gly - Leu - Gly - Gly - Gly - Gly - Gly - Gly | | |
| 46 - 46A | | 10 | 644.4 |
| | Gly - Leu - Gly - Gly - Gly - Gly - Gly - Gly - Gly | | |
| 47 - 47A | | 10 | 715.5 |
| | Leu - Gly - Gly - Gly - Gly - Gly - Gly - Gly - Lys | | |
| 48 - 48A | | 10 | 730.5 |
| | Gly - Gly - Gly - Gly - Gly - Gly - Gly - Lys - Lys | | |
| 49 - 49A | | 10 | 810.5 |
| | Gly - Gly - Gly - Gly - Gly - Gly - Gly - Lys - Lys - His | | |

FIG. 2D

CYCLE 0

CYCLE 1

G: 1 2 3 4 5 6 7 16 17 22 24 35 37 38 40 41 42 43 44
   45 46 47 (22/0)
L: 9 12 18 25 29 36 39 (7/0)
D: 20 21 26 28 (4/0)
N: 14 27 31 (3/0)
S: 8 10 11 (3/0)
M: 30 34 (2/0)
K: 48 49 (2/0)
P: 23 33 (2/0)
A: 13 15 (2/0)
E: 32 (1/0)
H: 19 (1/0)

CYCLE 2

G: 2 3 4 5 6 7 8 17 18 23 25 36 38 39 41 42 43 44 45
   46 47 48 (22/0)
L: 10 13 19 26 30 37 40 (7/0)
D: 21 22 27 29 (4/0)
N: 15 28 32 (3/0)
S: 9 11 12 (3/0)
A: 14 16 (2/0)
P: 24 34 (2/0)
M: 31 35 (2/0)
K: 49 (1/0)
E: 33 (1/0)
R: 1 (1/0)
H: 20 (1/0)

CYCLE 3

CYCLE 4

G: 4 5 6 7 8 9 10 19 20 25 27 38 40 41 43 44 45 46 47 48 49 (21/0)
L: 12 15 21 28 32 39 42 (7/0)
D: 23 24 29 31 (4/0)
S: 2 11 13 14 (4/0)
N: 17 30 34 (3/0)
A: 16 18 (2/0)
P: 26 36 (2/0)
M: 33 37 (2/0)
K: 1 (1/0)
E: 35 (1/0)
R: 3 (1/0)
H: 22 (1/0)

CYCLE 5

G: 1 5 6 7 8 9 10 11 20 21 26 28 39 41 42 44 45 46 47 48 49 (21/0)
L: 13 16 22 29 33 40 43 (7/0)
D: 24 25 30 32 (4/0)
S: 3 12 14 15 (4/0)
N: 18 31 35 (3/0)
A: 17 19 (2/0)
P: 27 37 (2/0)
M: 34 38 (2/0)
K: 2 (1/0)
E: 36 (1/0)
R: 4 (1/0)
H: 23 (1/0)

CYCLE 6

CYCLE 7

G: 1  3  7  8  9  10  11  12  13  22  23  28  30  41  43  44  46  47  48  49 (20/0)
L: 15  18  24  31  35  42  45 (7/0)
D: 26  27  32  34 (4/0)
S: 5  14  16  17 (4/0)
N: 20  33  37 (3/0)
A: 19  21 (2/0)
P: 29  39 (2/0)
R: 2  6 (2/0)
M: 36  40 (2/0)
E: 38 (1/0)
H: 25 (1/0)
K: 4 (1/0)

CYCLE 8

G: 2  4  8  9  10  11  12  13  14  23  24  29  31  42  44  45  47  48  49 (19/0)
L: 16  19  25  32  36  43  46 (7/0)
D: 27  28  33  35 (4/0)
S: 6  15  17  18 (4/0)
N: 21  34  38 (3/0)
M: 37  41 (2/0)
A: 20  22 (2/0)
P: 30  40 (2/0)
R: 3  7 (2/0)
E: 1  39 (2/0)
H: 26 (1/0)
K: 5 (1/0)

(18/1)

CYCLE 9

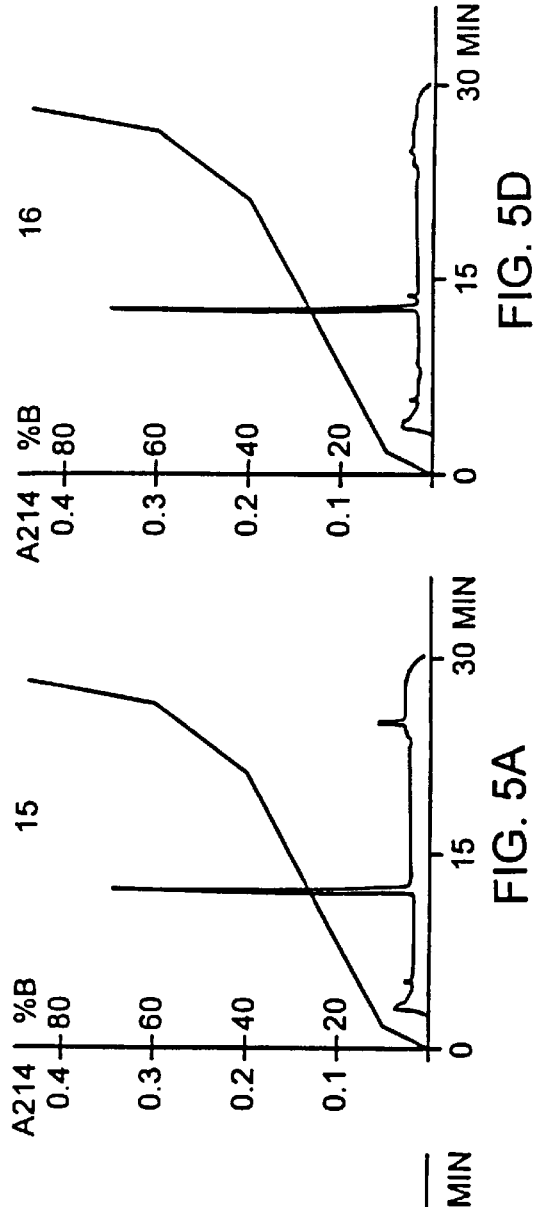
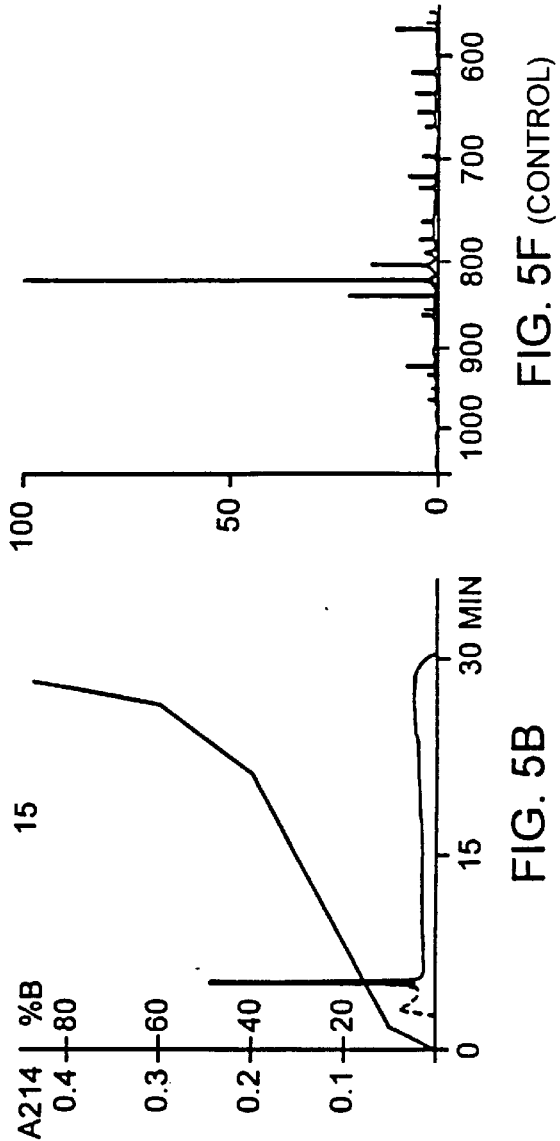
FIG. 5C  FIG. 5A  FIG. 5D
FIG. 5E  FIG. 5B  FIG. 5F (CONTROL)

APPARATUS AND METHODS FOR DETECTING ANTIBODIES

This is a division of application Ser. No. 07/978,674, filed Mar. 22, 1993 which is the National Phase of PCT/EP91/01529 filed Aug. 12, 1991 and P40 27 675/9 filed Aug. 31, 1990 on which priority is based.

BACKGROUND OF THE INVENTION

1. Field of the Invention

The invention relates to methods and apparatus for the detection of antibodies.

2. Brief Description of Related Art

Proteins play a decisive role in practically all biological processes such as enzymatic catalysis, transport and storage, coordinated movement, mechanical supporting function, immune protection, conduction of nerve stimuli and control of growth and differentiation. Proteins are made up of one of more linear polypeptide chains. Their multifarious functions are achieved through three-dimensional folding and the association of these chains. The folding and 3D structure is determined by the primary amino acid sequence of the chains. The multiplicity of protein structures in nature is produced by combining twenty amino acid components. Short partial sequences (oligopeptides) can to a certain extent imitate the local structure and function of a sequence in the total protein formation. Oligopeptides in turn can be prepared by chemical syntheses. Synthetic oligopeptides are thus an important aid in the analysis of the structure and function of proteins.

Because of the size and complexity of proteins, very many peptides are used in systematic studies. For example, localisation of a functional region within a relatively long protein chain using overlapping peptides (cf. M. Z. Atassi, Eur. J. Biol. 145, 1–20 (1984); H. M. Geysen, R. H. Meloen and S. J. Barteling, Proc. Natl. Acad. Sci. USA 81, 3998 (1984).

Also, deciphering the amino acid residues which are essential for function by means of substitution analysis (cf. R. A. Houghton, Proc. Natl. Acad. Sci. USA 82, 5131 (1985); H. M. Geysen, R. H. Meloen, and S. J. Barteling, Proc. Natl. Acad. Sci. USA 81, 3998 (1984).

Biological test reactions such as enzymatic reaction and antibody binding are very sensitive, so that even small quantities (ng to $\mu$g) of peptide substrates are sufficient. For the rapid and simple implementation of such tests it is advantageous if the peptide substrate is immobilized on a solid support material and can be readily removed from the reaction solution. The reaction with the peptide can then be measured quantitatively either in the remaining reaction solution or by subsequent analysis of the support-bound material.

The extent to which such systematic investigations can be carried out depends essentially on the speed of the peptide synthesis and on the technical and the chemical characteristics of the support. Rapid peptide syntheses can be carried out according to the principle developed by Merrifield of step-wise synthesis on a solid phase (R. B. Merrifield, J. Amer. Chem. Soc. 85, 2149 (1963)).

A process will be described below by which very many (several hundred) immobilized oligopeptides can advantageously be prepared per working day in quantities adequate for test purposes and on a suitable support material or flat material.

SUMMARY OF THE INVENTION

For this purpose, a process is provided according to the invention for the rapid synthesis of support-bound or free peptides, starting from one or more functionalized supports and synthesizing the required peptides step by step corresponding to the given amino acid sequences according to a suitable synthesis procedure, characterized in that flat material is used as the support for the coupling, small aliquots of a solution of the required amino acid or the required dipeptide or oligopeptide, in the form of their activated derivatives, are transferred to the planar support in the shape of spots or lines the coupling reaction is carried out in the reaction area which develops by wetting and where appropriate, the completed peptide is separated from the planar support using a suitable cleaving solution.

According to a special embodiment, several to very many different peptides are synthesized simultaneously alongside each other on a flat material on spot-shaped or linear reaction areas which are not in contact with each other.

According to a further special embodiment, the flat material employed is a porous or non-porous film, membrane, or a paper of this nature, which possess a chemically reactive functionality which is suitable for coupling amino acids or peptides.

BRIEF DESCRIPTION OF THE DRAWINGS

FIG. 1 is a representation of the primary amino acid residues sequence making up the immunogenic segment (CMV26) of the 36/40K protein of cytomegalovirus.

Figures 2D, 2E:
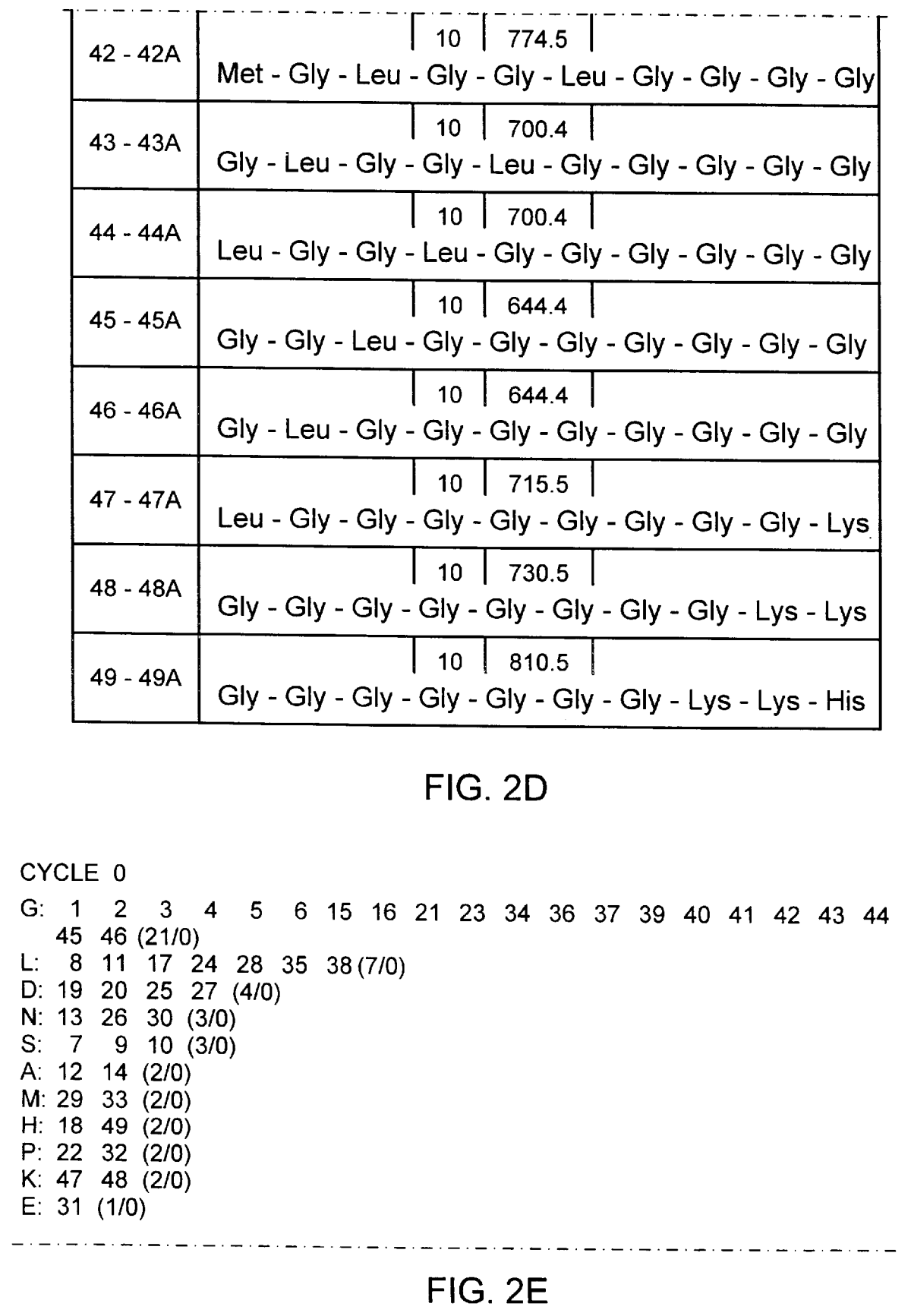
Figure 2F:
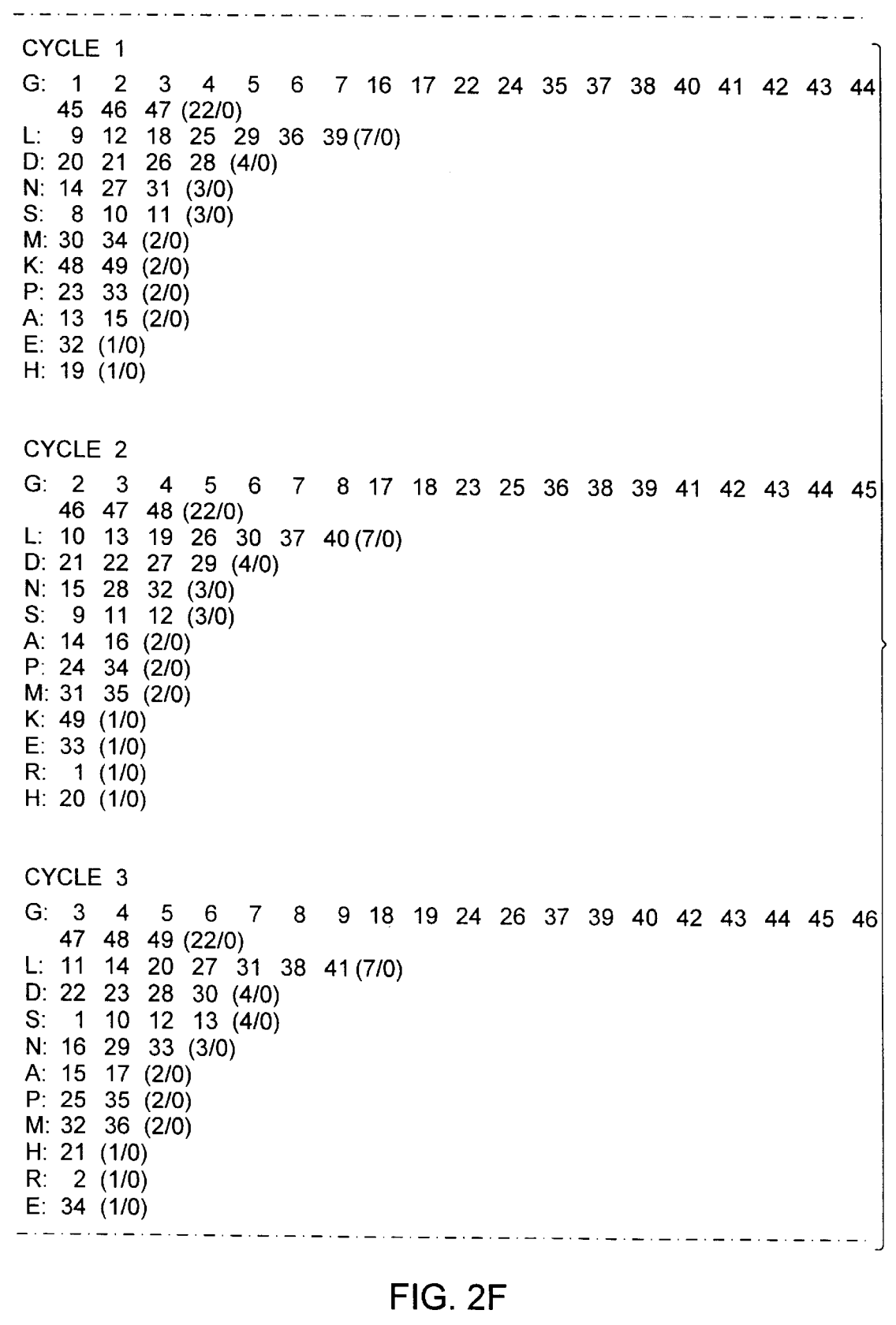
Figure 2G:
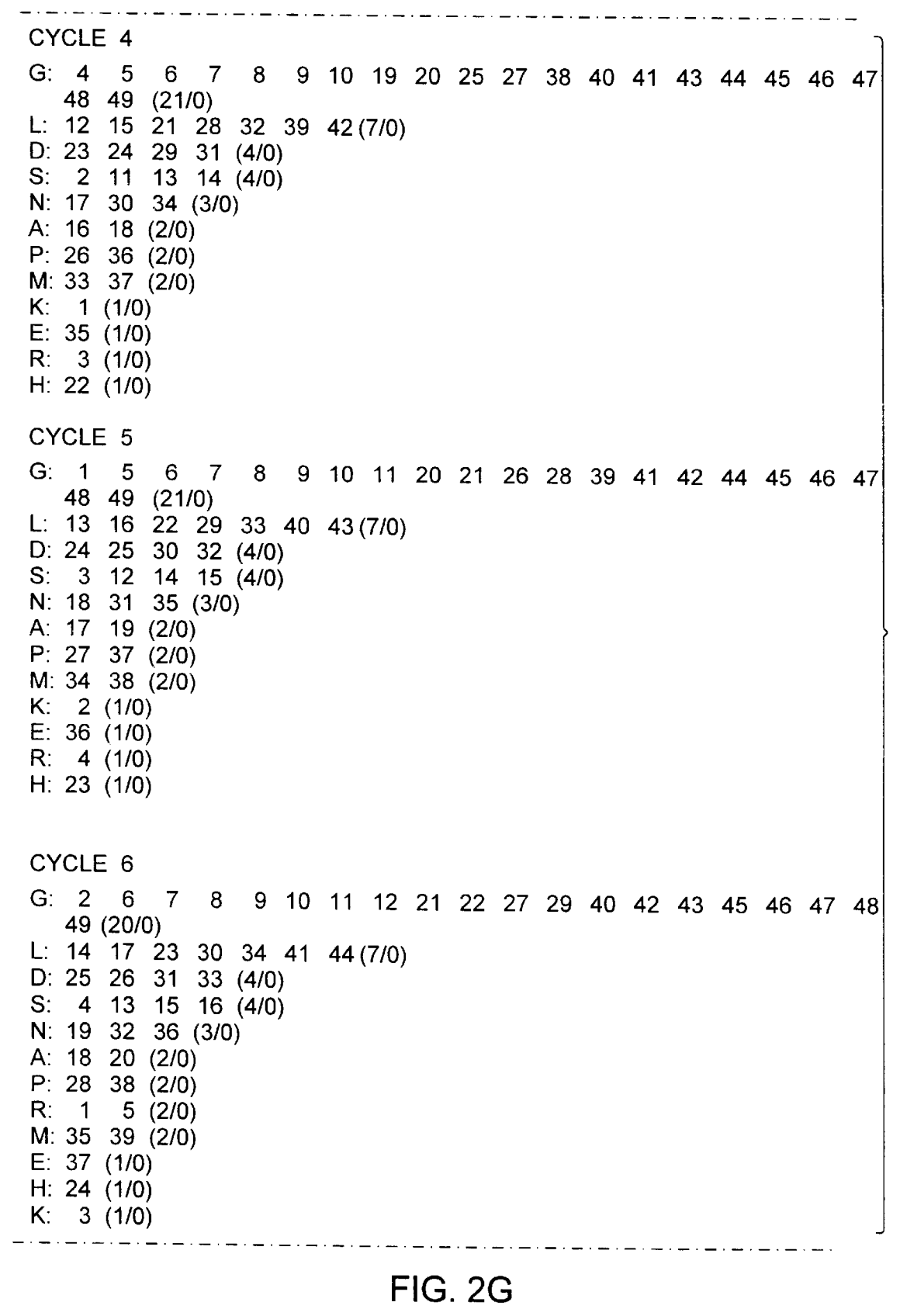
Figure 2H:
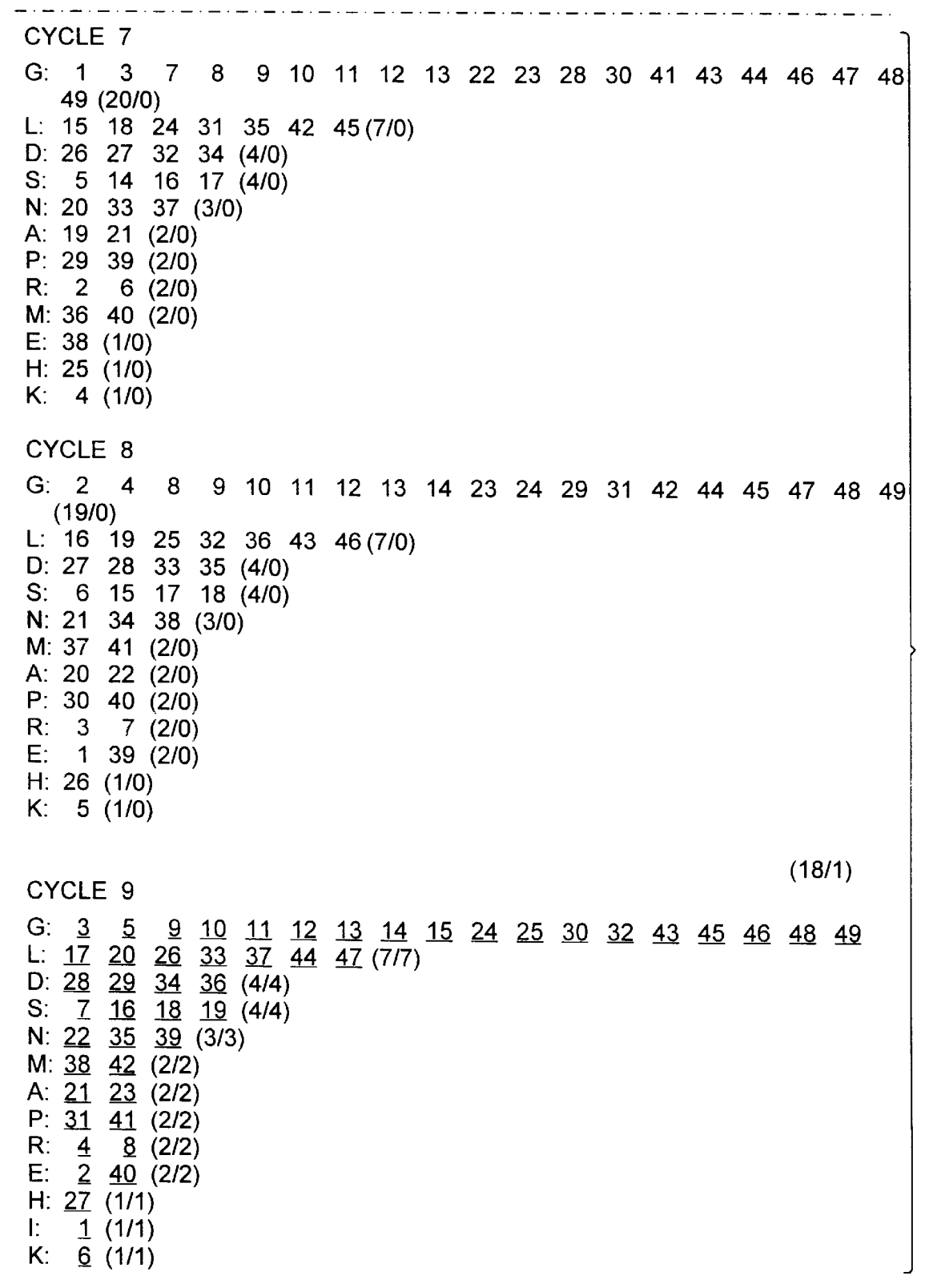

FIGS. 2A–H list all the decapeptides to be synthesized, with the allocated numbering and instructions for the simultaneous parallel implementation of the amino acid couplings.

FIG. 4 is an image of the flat cellulose support used in the process of the invention after a color test.

FIGS. 5A, 5C and 5D are depictions of HPLC traces of crude peptides Nos. 14, 15 and 16, respectively, prepared according to the invention.

FIGS. 5B, 5E and 5F show a FAB mass spectrum of peptides 15, 17 and a control, respectively (based on positive ions).

FIG. 6 shows a typical arrangement of patches on a paper sheet (B-Ala-B-Ala anchor stained with BPB).

DETAILED DESCRIPTION OF THE PREFERRED EMBODIMENTS OF THE INVENTION

Figure 3:
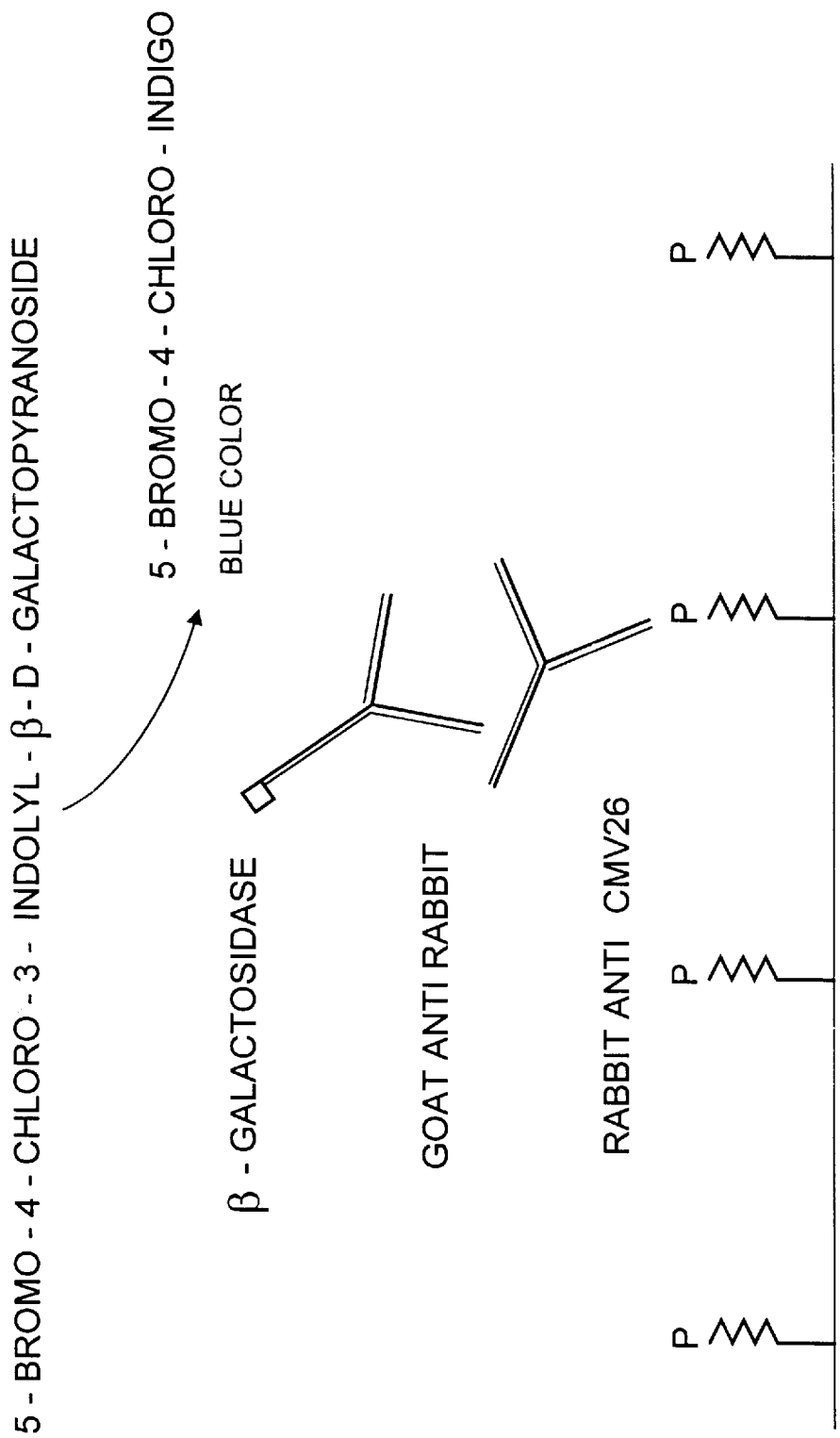
FIG. 3 is a schematic representation of the color test according to the process of the invention.

A mechanically stable flat material which is chemically inert towards the reagents and solvents employed is used as the support material. It can be porous or non-porous and can, as required, be placed on a base or be self-supporting. Materials which can be used are, for example, films, plates, membranes or papers. What is of importance is that the flat material bears chemically reactive groups (functionalities) to which the C-terminal components for peptide construction (suitably protected amino acids, dipeptides or oligopeptides) can be covalently linked.

It is advantageous if the support material which is employed for the chemical synthesis is also suitable for use in the biological test reactions. In this case, the peptides which have been prepared can be directly employed without isolation and subsequent immobilization, if the linkage between the peptide and the support material has been chosen so that it is stable against all the chemical reactions during the peptide synthesis.

If the support material is porous, its inner surface is also available for the synthesis. In this case, washing can also be performed by sucking solutions through the material. Non-porous support material has a very much smaller surface area. Washing can be performed by simple rinsing.

Suitable flat materials for peptide synthesis according to the claimed process are, for example, those composed of cellulose (which bear hydroxyl functionalities and can be employed directly), glass or plastics, such as polyethylene, polypropylene and Teflon, onto whose surface suitable chemical functionalities have been introduced, for example by graft polymerization of acrylic acid or its derivatives. The functionalization of the surfaces can additionally take place, for example, by the introduction of aminopropyl groups or glycine or diglycine anchor groups.

The size of the particular reaction area depends on the volume applied to the support, the absorptive properties of the support material and the volatility of the solvent. Depending on the selected support, for example on the specific functionality of a paper support, the particular magnitude of the fluid volume will naturally also depend on the chosen scale of the peptide synthesis. The magnitude of the particular fluid volume also determines the minimum distance between two reaction areas and thus, indirectly, the number of reaction areas which can be accommodated on a given support; cf., for example, Table 2.

In each case according to the nature and chemical pre-treatment of the support, the surface-specific loading with reactive functionalities may be varied over a wide range (e.g. 1 pmol to 1 $\mu$mol/cm$^2$).

Specific examples of papers which may be employed are Whatman Chrl, Whatman 540 and Whatman 3MM. Whatman 540 is preferable to Whatman Chrl because of its greater mechanical stability. The size of the sheet of paper, as well as the arrangement of the reaction areas or patches or spots, is arbitrary. Immunologists will prefer the format of a microtiter plate for 8× spots. In this case, a standard microtiter plate can be taken in which small holes have been bored in the centers of the wells and these standard microtiter plates can be used as templates for cutting out paper sheets (8.5×12.5 cm) and marking the positions of the spots with a pencil.

The peptides are then built up on the surface functionalities stepwise and corresponding to the predetermined sequences according to known methods for solid-phase peptide synthesis (E. Wünsch et al. in Houben-Wevl: Methoden der organischen Chemie (Methods of Organic Chemistry), 4th Edition, Volume 15 (E. Müller, Editor), Thieme, Stuttgart, 1974; G. Barany, R. B. Merrifield in The Peptides, Vol. 2 (E. Gross, U. Meienhofer, Eds; Academic Press, New York, 1970, p. 1). Preferably, the Fmoc/tBu method is adopted (C.-D. Chang, U. Meienhofer, Int. J. Peptide Protein Res. 11, 246 (1978); E. Atherton, H. Fox, D. Harkiss, C. J. Logan, R. C. Sheppard, B. J. Williams, J. Chem. Soc. Chem. Commun. 537 (1978). Besides the twenty essential amino acids, modified and non-natural amino acids may also be incorporated, as required.

The amino acid components (suitably protected and activated amino acid derivatives) which are necessary for the chemical synthesis of the peptides, are provided as concentrated solutions (0.1 to 0.3M) in a suitable solvent, which preferably has a high boiling point and low evaporation rate (e.g. N-methyl-pyrrolidinone, b.p. 203° C.), in small sealable receptacles.

The linking of amino acids to peptides takes place stepwise, beginning with the C-terminal end, and, where appropriate, in parallel for many peptides by the cyclical performance of the same two reaction steps on each occasion. The linking may be illustrated, for example, as follows:
1) Peptide bond formation: an aliquot (0.1 to 10 $\mu$l) of the activated amino acid solution is added to a predetermined dot or line on the planar support. As a result of wetting, a reaction area (patch) is formed which is defined by the volume applied. If many different peptides are to be synthesized in parallel on a correspondingly large support surface, the sites for application are located at distances which ensure that these reaction areas cannot intersect. The reaction time is 5 to 30 minutes, for example. After this, the support is washed several times, for example with dimethylformamide (DMF), in a suitable sealable receptacle or on a filtering device. The sites for application can be established by marking the support (e.g. pencil markings on cellulose paper). However, the free amine functionalities on the reaction surface may also be rendered directly visible by means of a color indicator (e,g. Bromphenol Blue; V. Krchnak, J. Vagner, P. Safar, M. Lebl, Collect. Czech. Chem. Commun. 53,2542 (1988) so that no other marking is necessary.
2) Elimination of the N-terminal protective group: for this purpose, the support is treated with sufficient cleavage solution. When the preferred Fmoc/tBu method is implemented, the Fmoc protective group is eliminated with 20 percent piperidine in DMF,. for example. After 2 to 10 minutes, for example, washing is carried out several times with DMF. Where appropriate, treatment is then carried out with a solution of the color indicator until the reaction areas become visible. Then washing is carried out several times with ethanol, for example, and the material is air-dried (where appropriate using a hairdryer at max. 40° C.

When all the peptide sequences have been completed, the N-terminal amino groups are preferably blocked, for example by acetylation with acetic anhydride. For this purpose, the support can be treated with acetylation solution (e.g. 5 percent acetic anhydride and 5 percent diisopropyl-ethylamine in DMF) and thereafter washed several times with DMF and ethanol.

After this, the protective groups on the amino acid side chains can be eliminated by a suitable acid treatment (depending on the chosen synthesis method). For this purpose, the support is treated with cleavage solution. According to a special embodiment using the Fmoc/tBu method (see the following list of amino acid derivatives employed), treatment is carried out, for example, for 10 minutes with 50 percent trifluoroacetic acid (TFA), 5 percent anisole and 1 percent thioanisole in dichloromethane. After that, the support is washed several times with dichloromethane, then DMF and then ethanol, and air-dried. The removal of the protective groups can also be achieved by treating with 50 percent TFA and 2 percent triisobutyl-silane in DCX in the course of about 60 min., after which washing is carried out, for example with DCM, DMF and ethanol.

The peptides are now prepared for biological use as immobilized substrates. For this, the support, with the peptides covalently bound to it, can either be treated as a whole, e.g. with a test reaction solution, or else the individual reaction areas can be separated by cutting up the sheet and then treated individually.

The simplest method for constructing peptides on supports in the manner described is to link the corresponding C-terminal amino acid components directly to the reactive functionalities on the support surface via stable amide or ester bonds. According to more specific embodiments, a so-called bifunctional linker reagent (cf. E. Atherton et al. J. Chem. Soc. Perkin Trans. I 538–546 (1981)) can first of all be linked to the support functionalities. The peptide, which is in turn constructed on it, can then, depending on the chemical nature of the peptide-linker bond, be cleaved off, e.g. under suitable reaction conditions with a C-terminal carboxyl or carboxamide group, and employed in soluble form for test purposes (labile linker ). However, the linker reagent may also be employed as a spacer, in order to increase the availability of the peptide for large reaction partners such as antibodies or enzymes (stable linker?).

When using paper supports, a two-step procedure may be employed.

First step (A): A uniform distribution of reactive amino functionalities is provided. For this purpose, the hydroxyl groups of the cellulose are usually esterified with an N-Fmoc-protected amino acid derivative and the amino groups are subsequently liberated by treatment with 20 percent piperidine solution in DMF.

Second step (B): A further N-Fmoc-amino acid is attached in a spot-shaped or linear manner to the amino functionalities which have been introduced. Subsequently, all the remaining amino functionalities are blocked by acetylation and the Fmoc is cleaved off.

Fmoc-glycine was also used for both derivatization steps within the scope of the present invention. However, not inconsiderable quantities of the Gly-Gly anchor were lost during removal of the Fmoc protective group and during extended storage, presumably as a result of diketopiperazine formation. Furthermore, the Gly-Gly end of the peptides appears to interfere with antibody binding, and some sera also appear to bind non-specifically to Ac-Gly-Gly. Fmoc-β-Ala is a better choice. β-Alanine is an unusual amino acid which is not present in natural proteins, while the β-Ala-β-Ala anchor is not subject to any diketopiperazine formation and the spacer is enlarged. Dried, flat materials which had been derivatized with patches of β-Ala-β-Ala and stained with BPB showed no loss of amino acid functionalities after several months of storage at −20° C. For more extended storage at temperatures up to 30° C., an Fmoc-protected anchor is even more stable. For clarification, the reader is referred to FIG. 6. This figure shows a typical arrangement of patches on a paper sheet (β-Ala-β-Ala anchor stained with BPB). In this case, the format conformed to that of a microtiter plate for 96 patches.

When compared to the state of the art (Geysen et al. 1984; Frank and Krause, German Patent Application P 39 35 572.1), the process which has been presented has the following advantages:

extremely simple operation; for the chemical couplings of the amino acid derivatives to peptides, only small volumes of the activated amino acid solutions need be dotted onto the planar support;

even smaller reaction volumes are possible, e.g. 0.1 to 1 μl, resulting in even more economical consumption of the expensive amino acid derivatives;

the supports such as cellulose papers or glass fiber papers are readily available or can be obtained commercially;

the scale of synthesis of individual peptides can be selected within a wide range because of the variable surface-specific loading with reactive functionalities;

the pipetting steps (in particular when the process is automated) can be carried out extremely quickly so that still more peptides can be prepared per unit time.

The process described above can also be enlisted in a corresponding manner for the rapid synthesis of support-bound or free oligonucleotides. With regard to the chemistry and the performance of oligonucleotide synthesis, reference can be made, for example, to the European Patent 84 100 059.9.

The process described here may also be automated. In this case, automatic pipetting devices can be employed for aliquotting and spotting of the activated amino acid solutions or nucleotide solutions as well as addition of the other washing and reaction solutions. The planar support must then be installed on an appropriate washing or filtering device.

The x/y-programmable TLC spotters or pipetting workstations which are obtainable commercially are suitable devices for the automated implementation of the process according to the invention. Volumes down to 10 nl can be added precisely at each desired location, so that several thousand peptides can be synthesized on a readily manageable flat material support. This is 2 orders of magnitude below the lithographic technique of Fodor et al. Sience, 251, 767–773 (1991). Even in the smallest quantities of fluid (about 10 nl), each peptide is formed in nmol quantities, which are sufficient for isolation and exhaustive characterisation.

IMPLEMENTATION EXAMPLE 1

Analysis of an immunogenic segment (CMV26) of the 36/40K protein of cytomegalovirus. FIG. 1: primary amino acid sequence of the cloned, immunogenic segment CMV26. Overlapping decapeptide sequences, in each case displaced by one amino acid, were derived from this. FIGS. 2 A–C: List of all the decapeptides to be synthesized with the allocated numbering and instructions for the simultaneous parallel implementation of the amino acid couplings.

Planar support: A 5.5×10.5 cm large sheet of cellulose paper (Chr1 or 540, Whatman, England) was cut out. 50 spots at a distance of 1 cm were then marked on it with pencil. The sheet was then placed in a cylindrical glass vessel which could be sealed with a ground stopper and treated at room temperature for 3 hours with 1 ml of a solution of 0.2M Fmoc-glycine 0.3M Hydroxybenzotriazole (HOBt)

0.24M Diisopropylcabodiimide (DIC)

0.2M N-methylimidazole (MeIm) in DMP, and subsequently washed three times with 10 ml of DMF on each occasion, then treated for 10 minutes with 20 percent piperidine in DMF (elimination of the Fmoc group), thereafter washed three times with 10 ml of DMF on each occasion and twice with 10 ml of ethanol (abs) on each occasion, and dried with a hairdryer. The quantity of glycine (free amino groups) esterified to the hydroxyl groups of the cellulose paper was determined quantitatively 0.2 as 0.3 μmol/cm².

The sheet was placed in a shallow glass or polyethylene dish. Aliquots (1 μl) of a solution of 0.3M Fmoc-glycine, 0.45M HOBt and 0.36M DICD in N-methyl-pyrolidinone (MPD) were then added to each of the pre-marked spots on the paper and the dish was covered with a glass plate. After 20 minutes, the sheet was placed in the glass cylinder and washed three times with 10 ml of DMF on each occasion. Then all the free amino groups of the first glycine coupling which were still present on the paper were blocked by acetylation. For this purpose, the sheet was treated for 10 minutes with 3 ml of 5 percent acetic anhydride and 5 percent diisopropylethylamine in DMF. Subsequently, it was washed three times with 10 ml of DMF on each occasion, then treated with 20 percent piperidine in DMF and washed three times again with DMF. After that, 3 ml of 0.3 percent Bromphenol Blue (BPB) in DMF were added, as a result of which the reaction areas of the 2nd glycine coupling stain blue. The sheet was then washed twice with 10 ml of ethanol on each occasion and dried.

The cellulose planar support which has been pretreated in this manner provides diglycine anchor groups with free primary amino functionalities at the marked reaction areas for the construction of peptides. The 49 decapeptides listed in FIG. 2A were numbered sequentially and synthesized simultaneously in parallel on the correspondingly numbered reaction areas as described above. The distribution of the activated amino acid solutions was carried out using the list shown in FIG. 2B and 2C.

Synthesis method: Fmoc/tBu method
Amino acid derivatives employed:
  Fmoc Ala
  Fmoc-Arg (Pmc)
  Fmoc-Asn (Tmob)
  Fmoc-Asp (OtBu)
  Fmoc-Cys (Butthio)
  Fmoc-Gln (Tmob)
  Fmoc-Glu (OtBu)
  Fmoc-Gly
  Fmoc-His (Boc)-Pfp
  Fmoc-Ile
  Fmoc-Leu
  Fmoc-Lys (Boc)
  Fmoc-Met
  Fmoc-Phe
  Fmoc-Pro
  Fmoc-Ser(tBu)
  Fmoc-Thr(tBu)
  Fmoc-Trp
  Fmoc-Tyr (tBu)
  Fmoc-Val All the protective groups of the amino acid side chains (-), with the exception of (Butthio) on Cys, can be removed with 20 to 50 percent TFA in dichloromethane. The Butthio group can then subsequently be removed with, for example, dithiothreitol (DTT) or dithioerythritol (DTE).

The activation of the amino acid derivatives can be effected according to standard methods, e.g. by 1.5-fold excess of 1-hydroxybenzotriazole (HOBt) and 1.2-fold excess of diisopropylcarbodiimide (DIC) in N-methylpyrrolidinone for one hour. Other activation methods, for example using symmetrical anhydrides, pentafluorophenol esters or BOP, are also possible. In accordance with the consumption that was calculated in advance, 0.2 to 1 ml of the solutions was made up. Aliquots of 1 $\mu$l were applied. After 5 to 20 minutes, the color of the reaction areas stained blue with BPB changed to yellow, indicating complete reaction of the free amino groups. Elimination of the Fmoc protective group was carried out using 20 percent piperidine in DMF for 5 minutes. Terminal acetylation of the completed peptides was achieved by treatment with 5 percent acetic anhydride and 5 percent diisopropylethylamine in DMF for 10 minutes. The protective groups on the amino acid side chains were removed using 20 percent TFA and 1 percent triisobutylsilane in dichloromethane for 20 minutes, and the support was subsequently washed, using on each occasion 10 ml portions, three times with dichloromethane, three times with DMF and three times with ethanol, and dried.

Using these peptides, the sequence-specific binding of anti-CMV26 antibodies in a rabbit serum, for example, was demonstrated by means of a color test.

FIG. 3: Schematic representation of the color test. The surface-bound peptides (P) are incubated with the rabbit anti-CMV26 serum, excess serum is washed off and incubation is then carried out with a goat anti-rabbit antibody, which is covalently linked to the enzyme $\beta$-galactosidase. Only if the anti-CMV26 antibodies can bind the peptide is the enzyme bound via the second antibody. This enzyme can then be detected by its activity in cleaving 5-bromo-4-chloro-3-indolyl-$\beta$-D-galactopyranoside, resulting, in the presence of a mild oxidising agent such as potassium hexacyanoferrate(III), in the formation of a blue indigo dye which is insoluble in water and alcohol.

Figures 4, 6:
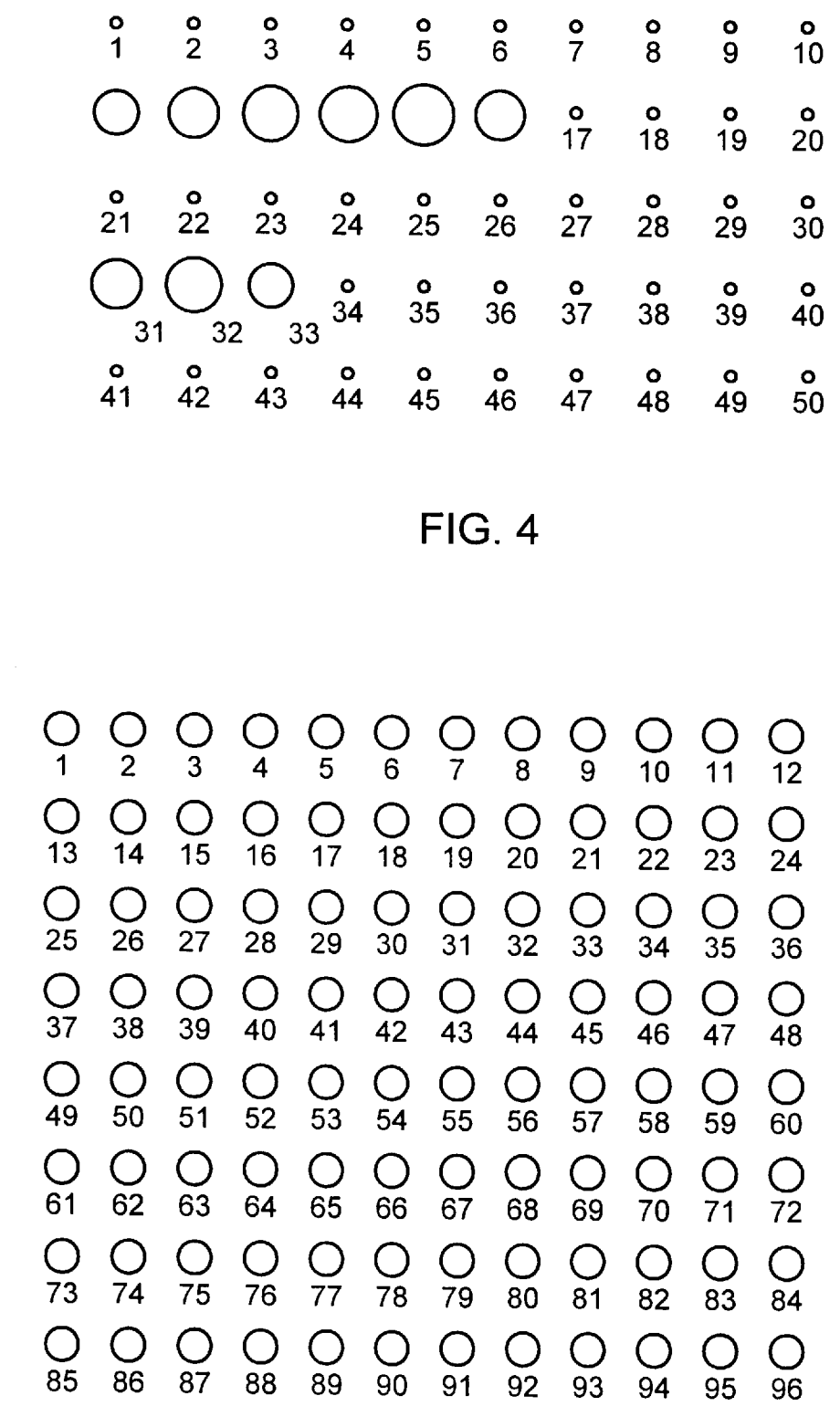

FIG. 4: Photograph of the flat cellulose support after the color test. The peptides on the reaction areas 11 to 16 and 30 to 33 are reacting positively.

The bound antibodies can be detached once more by treating the support with detergents (such as urea, sodium dodecyl sulfate and mercaptoethanol). The indigo dye can be washed off with DMF. After that the support with the immobilized peptides can be re-used. This can be repeated several times as long as no reaction conditions are used which detach or destroy the peptides. After more than ten antibody binding tests with the same support, some reaction areas were cut out and the peptides detached with 1M NaOH. It was possible unambiguously to detect the CMV26-Gly-Gly peptides both in HPLC analysis and by FAB mass spectroscopy.

IMPLEMENTATION EXAMPLE 2

Analysis of the same immunogenic segment (CMV26) of the 36/40K protein of cytomegalovirus. Planar support: A 5.5×10.5 cm large sheet of glass fiber paper (QM-A, Whatman, England) was cut out; 50 spots were then marked on it with a pencil at a distance of 1 cm in each case. The sheet was boiled overnight under reflux in a conical flask (250 ml) with a ground stopper together with 50 ml of 2 percent aminopropyl triethoxysilane in abs. toluene. Subsequently the sheet was washed three times with toluene and three times with acetone, on each occasion with portions of 10 ml, and dried at 110° C. for 1 hour. The aminopropyl groups (free amino groups) introduced in this manner were quantitatively estimated to be 30 to 50 nmol/cm$^2$.

All further chemical operations were carried out exactly as described in Implementation Example 1 for cellulose paper after the first glycine coupling. The result of the antibody binding test was identical.

The Implementation Examples 1 and 2 illustrate an important aspect of the use of the flat materials, with their bound peptides, which are prepared by the claimed process. They can be employed for diagnostic purposes in human and veterinary medicine for the very specific detection of bacterial and viral infections. Such infections lead, by immune reactions within the affected organism, to the formation of antibodies against viral or bacterial proteins. Using virus-specific or bacterium-specific peptides, such antibodies can be detected in the serum and the nature and subclass of the causative organism can thereby be determined. The same process can in turn be employed in order to identify the specific peptides, by (as shown in the implementation examples) preparing and testing series of peptides bound to flat material.

IMPLEMENTATION EXAMPLE 3

Four oligopeptides related to CMV26 were synthesized by spot-shaped synthesis on paper supports with Boc-Lys- Pro derivatization and cleaved from the supports using diketopiperazine formation. Details may be obtained from FIGS. 5 A–B and Table 1. These show:

FIGS. 5A, 5C and 5D depict HPLC traces of the crude peptides Nos. 14, 15 and 16, respectively, prepared according to the invention.

FIGS. 5B, 5E and 5F depict the FAB mass spectrum of peptides 15 and 17, respectively and a control (FIG. 5F) (based on positive ions);

TABLE 1

Tabulated data relating to beh synthesized peptides.

| Peptide No. | Sequence | Molecular mass[a] (theor.) | [M + H]+ | Amino acid analysis[b] D | S | G | A | L | P | K | Amount [nmol] |
|---|---|---|---|---|---|---|---|---|---|---|---|
| 14 | Ac—Gly—Gly—Ser—Leu—Ser—Ser—DKP (SEQ ID NO: 50) | 755.4 | 756.4 | — | 2.88 | 1.98 | — | 1.00 | x | x | 66 |
| 15 | Ac—Gly—Ser—Leu—Ser—Ser—Leu—DKP (SEQ ID NO: 51) | 811.4 | 812.4 | — | 2.90 | 0.97 | — | 2.00 | x | x | 52 |
| 16 | Ac—Ser—Leu—Ser—Ser—Leu—Ala—DKP (SEQ ID NO: 52) | 825.4 | 826.4 | — | 2.90 | — | 0.99 | 2.00 | x | x | 54 |
| 17 | Ac—Leu—Ser—Ser—Leu—Ala—Asn—DKP (SEQ ID NO: 53) | 852.4 | 853.4 | 0.89 | 1.98 | — | 1.00 | 2.00 | x | x | 57 |
| R | Ac-DKP | 268.2 | 267.2 | — | — | — | — | — | x | x | ca. 75 |

(a) Ac-DKP was determined in the FAB mass spectrum only as (M-H)− based on negative ions.

(b) The DKP moiety was not completely degraded under standard hydrolysis conditions; x signifies that Pro and Lys were present in equal quantities, although not equimolar in relation to the amino acid residues in the peptide chain.

IMPLEMENTATION EXAMPLE 4

Volumes down to 0.1 μl were dotted on by hand using an ordinary micropipette which was fitted with a polypropylene tip. Some typical data, which were obtained using two different paper qualities, are assembled in Table 2 below.

TABLE 2

Relation between dot volume, patch size and functionality.

| A: Whatman 540 | | β-ala anchor | B: Pre-treated Whatman 3 MM | | β-ala anchor |
|---|---|---|---|---|---|
| Volume [μl] | Diameter [mm] | Anchor [μmol] | Volume [μl] | Diameter [mm] | Anchor [μmol] |
| 0.1 | 3 | 0.02 | 1 | 4 | 0.10 |
| 0.5 | 5 | 0.7 | 5 | 7 | 0.45 |
| 1.0 | 7 | 0.13 | 10 | 10 | 0.85 |
| 2.0 | 9 | 0.25 | 20 | 14 | 1.70 |
| 5.0 | 12 | 0.60 | 50 | 22 | 4.40 |

Values are ± 5 percent

We claim:

1. A single, unitary, porous solid phase support having a planar surface, said surface having a plurality of separate, designated spotting zones, each spotting zone having bonded to the surface therein, the C-terminal ends of peptides, the peptides in adjacent spotting zones differing from each other in respect to the sequence of their amino acid residues, said sequences for said peptides being predetermined and known, wherein said support is obtained by a spotting method for the rapid synthesis of a plurality of peptides, said peptides differing from spot to spot from each other in the sequence of amino acid residues making up the peptides, which comprises;

providing a single, unitary, porous solid phase support having a planar surface, said surface bearing chemically reactive groups to which the C-terminal of a peptide under synthesis can be covalently bonded;

covalently bonding to the reactive groups in each freely selected discrete spotting zone, a starting amino acid residue of the sequence of each peptide to be synthesized by wetting each freely selected discrete spotting zone with a solution of an N-protected derivative of the starting amino acid residue, and synthesizing the different peptides by coupling additional amino acid residues to the starting amino acid residue, in a predetermined sequence, by wetting each predetermined discrete spotting zone with solutions of N-protected derivatives of the amino acids according to said predetermined sequence, whereby there is obtained a unitary, single solid phase support bearing a plurality of different, bound peptides.

2. The support of claim 1 wherein the surface is a cellulosic surface.

3. A method of detecting antibodies to bacterial or viral infections, in an analyte, which comprises;

providing the support of claim 1, wherein the plurality of peptides are known virus-specific or bacterial-specific proteins which will react with antibodies thereto;

contacting the spotting zones with the analyte for antibody determination; and observing the spotting zones for an immunoreaction, as an indication of antibody presence.

4. The support of claim 1 wherein the spotting zones are not in contact with each other.

5. The support of claim 1 wherein the solid phase support is paper.

6. The support of claim 1 wherein the solid phase support is an organic polymer.

7. The support of claim 1 wherein the solid phase support is glass.

8. The support of claim 1 wherein the solid phase support has a surface-specific loading with peptide molecules of 1 pmol to 1 $\mu$mol per $cm^2$.

9. The support of claim 1 wherein the wetting of each freely selected discrete spotting zone forms a line.

* * * * *

UNITED STATES PATENT AND TRADEMARK OFFICE
CERTIFICATE OF CORRECTION

PATENT NO. : 5,830,637

DATED : November 3, 1998

INVENTOR(S) : Ronald Frank and Sinan Guler

Page 1 of 2

It is certified that error appears in the above-indentified patent and that said Letters Patent is hereby corrected as shown below:

Col. 2, line 40; "and 5D" should read -- 5D and 5E -- .

Col. 2, line 41; "and 16" should read -- 16 and 17 -- .

Col. 2, line 43; "FIGS. 5B, 5E and 5Fshow" should read -- Fig. 5F shows.

Col. 2, between lines 45 and 46; there should be inserted -- Figure 5B is a depiction of a HPLC trace of a crude peptide R (reference) as a control -- .

Col. 9, line 4; "and 5D" should read -- 5D and 5E -- .

Col. 9, line 5; "and 16" should read -- 16 and 17 -- .

Col. 9, between lines 6 and 7; insert -- Figure 5B is a depiction of a HPLC trace of a crude peptide R (reference) as a control -- .

UNITED STATES PATENT AND TRADEMARK OFFICE
CERTIFICATE OF CORRECTION

PATENT NO. : 5,830,637
DATED : November 3, 1998
INVENTOR(S) : Ronald Frank and Sinan Guler It is certified that error appears in the above-identified patent and that said Letters Patent is hereby corrected as shown below:

Col. 9, line 7; replace "figs 5B, 5E and 5F depict" with -- Figure 5F depicts.

Col. 9, line 8; replace line 8 in its entirety with --peptide 15 --.

Signed and Sealed this

Fourth Day of May, 1999

*Attest:*

Q. TODD DICKINSON

*Attesting Officer*  Acting Commissioner of Patents and Trademarks

UNITED STATES PATENT AND TRADEMARK OFFICE
CERTIFICATE OF CORRECTION

PATENT NO. : 5,830,637
DATED : November 3, 1998
INVENTOR(S) : Ronald Frank and Sinan Guler It is certified that error appears in the above-identified patent and that said Letters Patent is hereby corrected as shown below:

On the title page: Item [54] and Column 1, line 1,
"SOLID PHASE SUPPORT WITH DIFFERENT PEPTIDES AND A METHOD FOR DETECTING ANTIBODIES"

Signed and Sealed this

Fourteenth Day of September, 1999

Attest:

Q. TODD DICKINSON

*Attesting Officer*     *Acting Commissioner of Patents and Trademarks*

SEQUENCE LISTING ( 1 ) GENERAL INFORMATION:

( i i i ) NUMBER OF SEQUENCES: 54

( 2 ) INFORMATION FOR SEQ ID NO: 1:

( i ) SEQUENCE CHARACTERISTICS:
        ( A ) LENGTH: 10 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:

( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:

( x i ) SEQUENCE DESCRIPTION: SEQ ID NO: 1:

Xaa  Glu  Gly  Arg  Gly  Lys  Ser  Arg  Gly  Gly
 1                    5                        1 0

( 2 ) INFORMATION FOR SEQ ID NO: 2:

( i ) SEQUENCE CHARACTERISTICS:
                ( A ) LENGTH: 10 residues
                ( B ) TYPE: amino acid
                ( C ) STRANDEDNESS:
                ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:

( x i ) SEQUENCE DESCRIPTION: SEQ ID NO: 2:

Glu  Gly  Arg  Gly  Lys  Ser  Arg  Gly  Gly  Gly
 1                    5                        1 0

( 2 ) INFORMATION FOR SEQ ID NO: 3:

( i ) SEQUENCE CHARACTERISTICS:
                ( A ) LENGTH: 10 residues
                ( B ) TYPE: amino acid
                ( C ) STRANDEDNESS:
                ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
                ( A ) ORGANISM:
                ( B ) STRAIN:
                ( C ) INDIVIDUAL ISOLATE:
                ( D ) DEVELOPMENTAL STAGE:
                ( E ) HAPLOTYPE:
                ( F ) TISSUE TYPE:
                ( G ) CELL TYPE:
                ( H ) CELL LINE:
                ( I ) ORGANELLE:

( v i i ) IMMEDIATE SOURCE:

( x i ) SEQUENCE DESCRIPTION: SEQ ID NO: 3:

Gly Arg Gly Lys Ser Arg Gly Gly Gly Gly
1               5                   10

(2) INFORMATION FOR SEQ ID NO: 4:

(i) SEQUENCE CHARACTERISTICS:
        (A) LENGTH: 10 residues
        (B) TYPE: amino acid
        (C) STRANDEDNESS:
        (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:

(xi) SEQUENCE DESCRIPTION: SEQ ID NO: 4:

Arg Gly Lys Ser Arg Gly Gly Gly Gly Gly
1               5                   10

(2) INFORMATION FOR SEQ ID NO: 5:

(i) SEQUENCE CHARACTERISTICS:
        (A) LENGTH: 10 residues
        (B) TYPE: amino acid
        (C) STRANDEDNESS:
        (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:

(xi) SEQUENCE DESCRIPTION: SEQ ID NO: 5:

Gly Lys Ser Arg Gly Gly Gly Gly Gly Gly
1               5                   10

(2) INFORMATION FOR SEQ ID NO: 6:

(i) SEQUENCE CHARACTERISTICS:
        (A) LENGTH: 10 residues
        (B) TYPE: amino acid (C) STRANDEDNESS:
(D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:

(xi) SEQUENCE DESCRIPTION: SEQ ID NO: 6:

Lys Ser Arg Gly Gly Gly Gly Gly Gly Gly
1               5                   10

(2) INFORMATION FOR SEQ ID NO: 7:

(i) SEQUENCE CHARACTERISTICS:
(A) LENGTH: 10 residues
(B) TYPE: amino acid
(C) STRANDEDNESS:
(D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:

(xi) SEQUENCE DESCRIPTION: SEQ ID NO: 7:

Ser Arg Gly Gly Gly Gly Gly Gly Gly Ser
1               5                   10

(2) INFORMATION FOR SEQ ID NO: 8:

(i) SEQUENCE CHARACTERISTICS:
(A) LENGTH: 10 residues
(B) TYPE: amino acid
(C) STRANDEDNESS:
(D) TOPOLOGY: LINEAR (ii) MOLECULE TYPE: Peptide (iii) HYPOTHETICAL:

(iv) ANTI-SENSE:

(v) FRAGMENT TYPE: internal fragment (v i) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(v i i) IMMEDIATE SOURCE:

(x i) SEQUENCE DESCRIPTION: SEQ ID NO: 8:

```
Arg Gly Gly Gly Gly Gly Gly Gly Ser Leu
1               5                   10
```

(2) INFORMATION FOR SEQ ID NO: 9:

(i) SEQUENCE CHARACTERISTICS:
        (A) LENGTH: 10 residues
        (B) TYPE: amino acid
        (C) STRANDEDNESS:
        (D) TOPOLOGY: LINEAR (i i) MOLECULE TYPE: Peptide (i i i) HYPOTHETICAL:

(i v) ANTI-SENSE:

(v) FRAGMENT TYPE: internal fragment (v i) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(v i i) IMMEDIATE SOURCE:

(x i) SEQUENCE DESCRIPTION: SEQ ID NO: 9:

```
Gly Gly Gly Gly Gly Gly Gly Ser Leu Ser
1               5                   10
```

(2) INFORMATION FOR SEQ ID NO: 10:

(i) SEQUENCE CHARACTERISTICS:
        (A) LENGTH: 10 residues
        (B) TYPE: amino acid
        (C) STRANDEDNESS:
        (D) TOPOLOGY: LINEAR (i i) MOLECULE TYPE: Peptide (i i i) HYPOTHETICAL:

(i v) ANTI-SENSE:

(v) FRAGMENT TYPE: internal fragment (v i) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:

( I ) ORGANELLE:

( v i i ) IMMEDIATE SOURCE:

( x i ) SEQUENCE DESCRIPTION: SEQ ID NO: 10:

```
Gly  Gly  Gly  Gly  Gly  Gly  Ser  Leu  Ser  Ser
1                  5                        10
```

( 2 ) INFORMATION FOR SEQ ID NO: 11:

( i ) SEQUENCE CHARACTERISTICS:
        ( A ) LENGTH: 10 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( x i ) SEQUENCE DESCRIPTION: SEQ ID NO: 11:

```
Gly  Gly  Gly  Gly  Gly  Ser  Leu  Ser  Ser  Leu
1                  5                        10
```

( 2 ) INFORMATION FOR SEQ ID NO: 12:

( i ) SEQUENCE CHARACTERISTICS:
        ( A ) LENGTH: 10 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( x i ) SEQUENCE DESCRIPTION: SEQ ID NO: 12:

```
Gly  Gly  Gly  Gly  Ser  Leu  Ser  Ser  Leu  Ala
1                  5                        10
```

(2) INFORMATION FOR SEQ ID NO: 13:

(i) SEQUENCE CHARACTERISTICS:
  (A) LENGTH: 10 residues
  (B) TYPE: amino acid
  (C) STRANDEDNESS:
  (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
  (A) ORGANISM:
  (B) STRAIN:
  (C) INDIVIDUAL ISOLATE:
  (D) DEVELOPMENTAL STAGE:
  (E) HAPLOTYPE:
  (F) TISSUE TYPE:
  (G) CELL TYPE:
  (H) CELL LINE:
  (I) ORGANELLE:

(vii) IMMEDIATE SOURCE:

(xi) SEQUENCE DESCRIPTION: SEQ ID NO: 13:

Gly Gly Gly Ser Leu Ser Ser Leu Ala Xaa
1               5                   10

(2) INFORMATION FOR SEQ ID NO: 14:

(i) SEQUENCE CHARACTERISTICS:
  (A) LENGTH: 10 residues
  (B) TYPE: amino acid
  (C) STRANDEDNESS:
  (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
  (A) ORGANISM:
  (B) STRAIN:
  (C) INDIVIDUAL ISOLATE:
  (D) DEVELOPMENTAL STAGE:
  (E) HAPLOTYPE:
  (F) TISSUE TYPE:
  (G) CELL TYPE:
  (H) CELL LINE:
  (I) ORGANELLE:

(vii) IMMEDIATE SOURCE:

(xi) SEQUENCE DESCRIPTION: SEQ ID NO: 14:

Gly Gly Ser Leu Ser Ser Leu Ala Xaa Ala
1               5                   10

(2) INFORMATION FOR SEQ ID NO: 15:

(i) SEQUENCE CHARACTERISTICS:
  (A) LENGTH: 10 residues
  (B) TYPE: amino acid
  (C) STRANDEDNESS:
  (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:

(xi) SEQUENCE DESCRIPTION: SEQ ID NO: 15:

Gly Ser Leu Ser Ser Leu Ala Xaa Ala Gly
1               5                   10

(2) INFORMATION FOR SEQ ID NO: 16:

(i) SEQUENCE CHARACTERISTICS:
    (A) LENGTH: 10 residues
    (B) TYPE: amino acid
    (C) STRANDEDNESS:
    (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:

(xi) SEQUENCE DESCRIPTION: SEQ ID NO: 16:

Ser Leu Ser Ser Leu Ala Xaa Ala Gly Gly
1               5                   10

(2) INFORMATION FOR SEQ ID NO: 17:

(i) SEQUENCE CHARACTERISTICS:
    (A) LENGTH: 10 residues
    (B) TYPE: amino acid
    (C) STRANDEDNESS:
    (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
    (A) ORGANISM:
    (B) STRAIN:
    (C) INDIVIDUAL ISOLATE:

(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:

(xi) SEQUENCE DESCRIPTION: SEQ ID NO: 17:

Leu Ser Ser Leu Ala Xaa Ala Gly Gly Leu
1               5                   10

(2) INFORMATION FOR SEQ ID NO: 18:

(i) SEQUENCE CHARACTERISTICS:
(A) LENGTH: 10 residues
(B) TYPE: amino acid
(C) STRANDEDNESS:
(D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:

(xi) SEQUENCE DESCRIPTION: SEQ ID NO: 18:

Ser Ser Leu Ala Xaa Ala Gly Gly Leu His
1               5                   10

(2) INFORMATION FOR SEQ ID NO: 19:

(i) SEQUENCE CHARACTERISTICS:
(A) LENGTH: 10 residues
(B) TYPE: amino acid
(C) STRANDEDNESS:
(D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:

(xi) SEQUENCE DESCRIPTION: SEQ ID NO: 19:

Ser Leu Ala Xaa Ala Gly Gly Leu His Asp
1               5                   10

(2) INFORMATION FOR SEQ ID NO: 20:

(i) SEQUENCE CHARACTERISTICS:
        (A) LENGTH: 10 residues
        (B) TYPE: amino acid
        (C) STRANDEDNESS:
        (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:

(xi) SEQUENCE DESCRIPTION: SEQ ID NO: 20:

Leu Ala Xaa Ala Gly Gly Leu His Asp Asp
1               5                   10

(2) INFORMATION FOR SEQ ID NO: 21:

(i) SEQUENCE CHARACTERISTICS:
        (A) LENGTH: 10 residues
        (B) TYPE: amino acid
        (C) STRANDEDNESS:
        (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:

(xi) SEQUENCE DESCRIPTION: SEQ ID NO: 21:

Ala Xaa Ala Gly Gly Leu His Asp Asp Gly
1               5                   10

(2) INFORMATION FOR SEQ ID NO: 22:

(i) SEQUENCE CHARACTERISTICS:
        (A) LENGTH: 10 residues
        (B) TYPE: amino acid (C) STRANDEDNESS:
(D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:

(xi) SEQUENCE DESCRIPTION: SEQ ID NO: 22:

```
Xaa  Ala  Gly  Gly  Leu  His  Asp  Asp  Gly  Pro
 1                    5                        10
```

(2) INFORMATION FOR SEQ ID NO: 23:

(i) SEQUENCE CHARACTERISTICS:
(A) LENGTH: 10 residues
(B) TYPE: amino acid
(C) STRANDEDNESS:
(D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:

(xi) SEQUENCE DESCRIPTION: SEQ ID NO: 23:

```
Ala  Gly  Gly  Leu  His  Asp  Asp  Gly  Pro  Gly
 1                    5                        10
```

(2) INFORMATION FOR SEQ ID NO: 24:

(i) SEQUENCE CHARACTERISTICS:
(A) LENGTH: 10 residues
(B) TYPE: amino acid
(C) STRANDEDNESS:
(D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:

(xi) SEQUENCE DESCRIPTION: SEQ ID NO: 24:

```
Gly Gly Leu His Asp Asp Gly Pro Gly Leu
 1               5                  10
```

(2) INFORMATION FOR SEQ ID NO: 25:

(i) SEQUENCE CHARACTERISTICS:
    (A) LENGTH: 10 residues
    (B) TYPE: amino acid
    (C) STRANDEDNESS:
    (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:

(xi) SEQUENCE DESCRIPTION: SEQ ID NO: 25:

```
Gly Leu His Asp Asp Gly Pro Gly Leu Asp
 1               5                  10
```

(2) INFORMATION FOR SEQ ID NO: 26:

(i) SEQUENCE CHARACTERISTICS:
    (A) LENGTH: 10 residues
    (B) TYPE: amino acid
    (C) STRANDEDNESS:
    (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:

( I ) ORGANELLE:

( v i i ) IMMEDIATE SOURCE:

( x i ) SEQUENCE DESCRIPTION: SEQ ID NO: 26:

```
Leu His Asp Asp Gly Pro Gly Leu Asp Xaa
1               5                   10
```

( 2 ) INFORMATION FOR SEQ ID NO: 27:

( i ) SEQUENCE CHARACTERISTICS:
        ( A ) LENGTH: 10 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( x i ) SEQUENCE DESCRIPTION: SEQ ID NO: 27:

```
His Asp Asp Gly Pro Gly Leu Asp Xaa Asp
1               5                   10
```

( 2 ) INFORMATION FOR SEQ ID NO: 28:

( i ) SEQUENCE CHARACTERISTICS:
        ( A ) LENGTH: 10 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( x i ) SEQUENCE DESCRIPTION: SEQ ID NO: 28:

```
Asp Asp Gly Pro Gly Leu Asp Xaa Asp Leu
1               5                   10
```

(2) INFORMATION FOR SEQ ID NO: 29:

(i) SEQUENCE CHARACTERISTICS:
        (A) LENGTH: 10 residues
        (B) TYPE: amino acid
        (C) STRANDEDNESS:
        (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:

(xi) SEQUENCE DESCRIPTION: SEQ ID NO: 29:

Asp Gly Pro Gly Leu Asp Xaa Asp Leu Met
1               5                   10

(2) INFORMATION FOR SEQ ID NO: 30:

(i) SEQUENCE CHARACTERISTICS:
        (A) LENGTH: 10 residues
        (B) TYPE: amino acid
        (C) STRANDEDNESS:
        (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:

(xi) SEQUENCE DESCRIPTION: SEQ ID NO: 30:

Gly Pro Gly Leu Asp Xaa Asp Leu Met Xaa
1               5                   10

(2) INFORMATION FOR SEQ ID NO: 31:

(i) SEQUENCE CHARACTERISTICS:
        (A) LENGTH: 10 residues
        (B) TYPE: amino acid
        (C) STRANDEDNESS:
        (D) TOPOLOGY: LINEAR (ii) MOLECULE TYPE: Peptide (  i i i ) HYPOTHETICAL:

(  i v ) ANTI-SENSE:

(  v ) FRAGMENT TYPE: internal fragment (  v i ) ORIGINAL SOURCE:
- ( A ) ORGANISM:
- ( B ) STRAIN:
- ( C ) INDIVIDUAL ISOLATE:
- ( D ) DEVELOPMENTAL STAGE:
- ( E ) HAPLOTYPE:
- ( F ) TISSUE TYPE:
- ( G ) CELL TYPE:
- ( H ) CELL LINE:
- ( I ) ORGANELLE:

(  v i i ) IMMEDIATE SOURCE:

(  x i ) SEQUENCE DESCRIPTION: SEQ ID NO: 31:

Pro Gly Leu Asp Xaa Asp Leu Met Xaa Glu
1               5                   1 0

( 2 ) INFORMATION FOR SEQ ID NO: 32:

(  i ) SEQUENCE CHARACTERISTICS:
- ( A ) LENGTH: 10 residues
- ( B ) TYPE: amino acid
- ( C ) STRANDEDNESS:
- ( D ) TOPOLOGY: LINEAR (  i i ) MOLECULE TYPE: Peptide (  i i i ) HYPOTHETICAL:

(  i v ) ANTI-SENSE:

(  v ) FRAGMENT TYPE: internal fragment (  v i ) ORIGINAL SOURCE:
- ( A ) ORGANISM:
- ( B ) STRAIN:
- ( C ) INDIVIDUAL ISOLATE:
- ( D ) DEVELOPMENTAL STAGE:
- ( E ) HAPLOTYPE:
- ( F ) TISSUE TYPE:
- ( G ) CELL TYPE:
- ( H ) CELL LINE:
- ( I ) ORGANELLE:

(  v i i ) IMMEDIATE SOURCE:

(  x i ) SEQUENCE DESCRIPTION: SEQ ID NO: 32:

Gly Leu Asp Xaa Asp Leu Met Xaa Glu Pro
1               5                   1 0

( 2 ) INFORMATION FOR SEQ ID NO: 33:

(  i ) SEQUENCE CHARACTERISTICS:
- ( A ) LENGTH: 10 residues
- ( B ) TYPE: amino acid
- ( C ) STRANDEDNESS:
- ( D ) TOPOLOGY: LINEAR (  i i ) MOLECULE TYPE: Peptide (  i i i ) HYPOTHETICAL:

(  i v ) ANTI-SENSE:

(  v ) FRAGMENT TYPE: internal fragment (  v i ) ORIGINAL SOURCE:
- ( A ) ORGANISM:
- ( B ) STRAIN:
- ( C ) INDIVIDUAL ISOLATE:

(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:

(xi) SEQUENCE DESCRIPTION: SEQ ID NO: 33:

Leu Asp Xaa Asp Leu Met Xaa Glu Pro Met
1               5                       10

(2) INFORMATION FOR SEQ ID NO: 34:

(i) SEQUENCE CHARACTERISTICS:
(A) LENGTH: 10 residues
(B) TYPE: amino acid
(C) STRANDEDNESS:
(D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:

(xi) SEQUENCE DESCRIPTION: SEQ ID NO: 34:

Asp Xaa Asp Leu Met Xaa Glu Pro Met Gly
1               5                       10

(2) INFORMATION FOR SEQ ID NO: 35:

(i) SEQUENCE CHARACTERISTICS:
(A) LENGTH: 10 residues
(B) TYPE: amino acid
(C) STRANDEDNESS:
(D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
(A) ORGANISM:
(B) STRAIN:
(C) INDIVIDUAL ISOLATE:
(D) DEVELOPMENTAL STAGE:
(E) HAPLOTYPE:
(F) TISSUE TYPE:
(G) CELL TYPE:
(H) CELL LINE:
(I) ORGANELLE:

(vii) IMMEDIATE SOURCE:

(xi) SEQUENCE DESCRIPTION: SEQ ID NO: 35:

```
Xaa  Asp  Leu  Met  Xaa  Glu  Pro  Met  Gly  Leu
 1                  5                       10
```

( 2 ) INFORMATION FOR SEQ ID NO: 36:

( i ) SEQUENCE CHARACTERISTICS:
        ( A ) LENGTH: 10 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( x i ) SEQUENCE DESCRIPTION: SEQ ID NO: 36:

```
Asp  Leu  Met  Xaa  Glu  Pro  Met  Gly  Leu  Gly
 1                  5                       10
```

( 2 ) INFORMATION FOR SEQ ID NO: 37:

( i ) SEQUENCE CHARACTERISTICS:
        ( A ) LENGTH: 10 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( x i ) SEQUENCE DESCRIPTION: SEQ ID NO: 37:

```
Leu  Met  Xaa  Glu  Pro  Met  Gly  Leu  Gly  Gly
 1                  5                       10
```

( 2 ) INFORMATION FOR SEQ ID NO: 38:

( i ) SEQUENCE CHARACTERISTICS:
        ( A ) LENGTH: 10 residues
        ( B ) TYPE: amino acid ( C ) STRANDEDNESS:
            ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:

( x i ) SEQUENCE DESCRIPTION: SEQ ID NO: 38:

Met  Xaa  Glu  Pro  Met  Gly  Leu  Gly  Gly  Leu
 1                     5                    1 0

( 2 ) INFORMATION FOR SEQ ID NO: 39:

( i ) SEQUENCE CHARACTERISTICS:
            ( A ) LENGTH: 10 residues
            ( B ) TYPE: amino acid
            ( C ) STRANDEDNESS:
            ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:

( x i ) SEQUENCE DESCRIPTION: SEQ ID NO: 39:

Xaa  Glu  Pro  Met  Gly  Leu  Gly  Gly  Leu  Gly
 1                     5                    1 0

( 2 ) INFORMATION FOR SEQ ID NO: 40:

( i ) SEQUENCE CHARACTERISTICS:
            ( A ) LENGTH: 10 residues
            ( B ) TYPE: amino acid
            ( C ) STRANDEDNESS:
            ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:

( x i ) SEQUENCE DESCRIPTION: SEQ ID NO: 40:

Glu Pro Met Gly Leu Gly Gly Leu Gly Gly
1               5                   10

( 2 ) INFORMATION FOR SEQ ID NO: 41:

( i ) SEQUENCE CHARACTERISTICS:
    ( A ) LENGTH: 10 residues
    ( B ) TYPE: amino acid
    ( C ) STRANDEDNESS:
    ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:

( x i ) SEQUENCE DESCRIPTION: SEQ ID NO: 41:

Pro Met Gly Leu Gly Gly Leu Gly Gly Gly
1               5                   10

( 2 ) INFORMATION FOR SEQ ID NO: 42:

( i ) SEQUENCE CHARACTERISTICS:
    ( A ) LENGTH: 10 residues
    ( B ) TYPE: amino acid
    ( C ) STRANDEDNESS:
    ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:

( I ) ORGANELLE:

( v i i ) IMMEDIATE SOURCE:

( x i ) SEQUENCE DESCRIPTION: SEQ ID NO: 42:

Met Gly Leu Gly Gly Leu Gly Gly Gly Gly
1               5                   10

( 2 ) INFORMATION FOR SEQ ID NO: 43:

( i ) SEQUENCE CHARACTERISTICS:
        ( A ) LENGTH: 10 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( x i ) SEQUENCE DESCRIPTION: SEQ ID NO: 43:

Gly Leu Gly Gly Leu Gly Gly Gly Gly Gly
1               5                   10

( 2 ) INFORMATION FOR SEQ ID NO: 44:

( i ) SEQUENCE CHARACTERISTICS:
        ( A ) LENGTH: 10 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( x i ) SEQUENCE DESCRIPTION: SEQ ID NO: 44:

Leu Gly Gly Leu Gly Gly Gly Gly Gly Gly
1               5                   10

(2) INFORMATION FOR SEQ ID NO: 45:

(i) SEQUENCE CHARACTERISTICS:
        (A) LENGTH: 10 residues
        (B) TYPE: amino acid
        (C) STRANDEDNESS:
        (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:

(xi) SEQUENCE DESCRIPTION: SEQ ID NO: 45:

Gly Gly Leu Gly Gly Gly Gly Gly Gly Gly
1                  5                       10

(2) INFORMATION FOR SEQ ID NO: 46:

(i) SEQUENCE CHARACTERISTICS:
        (A) LENGTH: 10 residues
        (B) TYPE: amino acid
        (C) STRANDEDNESS:
        (D) TOPOLOGY: LINEAR (ii) MOLECULE TYPE: Peptide (iii) HYPOTHETICAL:

(iv) ANTI-SENSE:

(v) FRAGMENT TYPE: internal fragment (vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:

(xi) SEQUENCE DESCRIPTION: SEQ ID NO: 46:

Gly Leu Gly Gly Gly Gly Gly Gly Gly Gly
1                  5                       10

(2) INFORMATION FOR SEQ ID NO: 47:

(i) SEQUENCE CHARACTERISTICS:
        (A) LENGTH: 10 residues
        (B) TYPE: amino acid
        (C) STRANDEDNESS:
        (D) TOPOLOGY: LINEAR (ii) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:

( x i ) SEQUENCE DESCRIPTION: SEQ ID NO: 47:

Leu Gly Gly Gly Gly Gly Gly Gly Gly Lys
1               5                   10

( 2 ) INFORMATION FOR SEQ ID NO: 48:

( i ) SEQUENCE CHARACTERISTICS:
        ( A ) LENGTH: 10 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( x i ) SEQUENCE DESCRIPTION: SEQ ID NO: 48:

Gly Gly Gly Gly Gly Gly Gly Gly Lys Lys
1               5                   10

( 2 ) INFORMATION FOR SEQ ID NO: 49:

( i ) SEQUENCE CHARACTERISTICS:
        ( A ) LENGTH: 10 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:

( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( v i i ) IMMEDIATE SOURCE:

( x i ) SEQUENCE DESCRIPTION: SEQ ID NO: 49:

Gly Gly Gly Gly Gly Gly Gly Lys Lys His
1               5                   10

( 2 ) INFORMATION FOR SEQ ID NO: 50:

( i ) SEQUENCE CHARACTERISTICS:
( A ) LENGTH: 6 residues
( B ) TYPE: amino acid
( C ) STRANDEDNESS:
( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
( A ) ORGANISM:
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( v i i ) IMMEDIATE SOURCE:

( x i ) SEQUENCE DESCRIPTION: SEQ ID NO: 50:

Gly Gly Ser Leu Ser Ser
1               5

( 2 ) INFORMATION FOR SEQ ID NO: 51:

( i ) SEQUENCE CHARACTERISTICS:
( A ) LENGTH: 6 residues
( B ) TYPE: amino acid
( C ) STRANDEDNESS:
( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
( A ) ORGANISM:
( B ) STRAIN:
( C ) INDIVIDUAL ISOLATE:
( D ) DEVELOPMENTAL STAGE:
( E ) HAPLOTYPE:
( F ) TISSUE TYPE:
( G ) CELL TYPE:
( H ) CELL LINE:
( I ) ORGANELLE:

( v i i ) IMMEDIATE SOURCE:

( x i ) SEQUENCE DESCRIPTION: SEQ ID NO: 51:

```
Gly  Ser  Leu  Ser  Ser  Leu
 1                 5
```

( 2 ) INFORMATION FOR SEQ ID NO: 52:

( i ) SEQUENCE CHARACTERISTICS:
        ( A ) LENGTH: 6 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( x i ) SEQUENCE DESCRIPTION: SEQ ID NO: 52:

```
Ser  Leu  Ser  Ser  Leu  Ala
 1                 5
```

( 2 ) INFORMATION FOR SEQ ID NO: 53:

( i ) SEQUENCE CHARACTERISTICS:
        ( A ) LENGTH: 6 residues
        ( B ) TYPE: amino acid
        ( C ) STRANDEDNESS:
        ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:

( x i ) SEQUENCE DESCRIPTION: SEQ ID NO: 53:

```
Leu  Ser  Ser  Leu  Ala  Xaa
 1                 5
```

( 2 ) INFORMATION FOR SEQ ID NO: 54:

( i ) SEQUENCE CHARACTERISTICS:
        ( A ) LENGTH: 70 residues
        ( B ) TYPE: amino acid -continued

```
     ( C ) STRANDEDNESS:
     ( D ) TOPOLOGY: LINEAR ( i i ) MOLECULE TYPE: Peptide ( i i i ) HYPOTHETICAL:

( i v ) ANTI-SENSE:

( v ) FRAGMENT TYPE: internal fragment ( v i ) ORIGINAL SOURCE:
          ( A ) ORGANISM:
          ( B ) STRAIN:
          ( C ) INDIVIDUAL ISOLATE:
          ( D ) DEVELOPMENTAL STAGE:
          ( E ) HAPLOTYPE:
          ( F ) TISSUE TYPE:
          ( G ) CELL TYPE:
          ( H ) CELL LINE:
          ( I ) ORGANELLE:

( v i i ) IMMEDIATE SOURCE:

( x i ) SEQUENCE DESCRIPTION: SEQ ID NO: 54:

Ala  Arg  Gly  Ser  Xaa  Glu  Arg  Gly  Lys  Ser  Arg  Gly  Gly
 1               5                         10

Gly  Gly  Gly  Gly  Gly  Ser  Leu  Ser  Ser  Leu  Ala
      15                    20

Xaa  Ala  Gly  Gly  Leu  Asn  Asp  Asp  Gly  Pro  Gly
 25                      30                        35

Asp  Xaa  Asp  Leu  Met  Xaa  Glu  Pro  Met  Gly  Leu
                40                           45

Gly  Gly  Leu  Gly  Gly  Gly  Gly  Gly  Gly  Gly  Gly  Lys  Lys
             50                      55

His  Leu  Asp  Pro  Ser  Thr  Cys  Ser  Gln  Ala  Cys
 60                    65                        70
```